United States Patent [19]

Chaihorsky

[11] Patent Number: 5,670,632
[45] Date of Patent: Sep. 23, 1997

[54] PROCESS FOR OBTAINING AN ISOFLAVONE CONCENTRATE FROM A SOYBEAN EXTRACT

[75] Inventor: Abas Chaihorsky, Sparks, Nev.

[73] Assignee: ACDS Technologies, Ltd., Sparks, Nev.

[21] Appl. No.: 588,199

[22] Filed: Jan. 18, 1996

[51] Int. Cl.$^6$ .................................................. C07H 17/07
[52] U.S. Cl. ................... 536/8; 549/403; 536/7.5
[58] Field of Search ........................ 549/403; 536/7.5, 536/8

[56] References Cited

U.S. PATENT DOCUMENTS

| | | |
|---|---|---|
| 4,428,876 | 1/1984 | Iwamura . |
| 4,960,908 | 10/1990 | Ito . |
| 5,247,102 | 9/1993 | Kallay . |
| 5,424,331 | 6/1995 | Shlyankevich . |

*Primary Examiner*—Nicky Chan
*Attorney, Agent, or Firm*—Herbert Dubno; Jonathan Myers

[57] ABSTRACT

A process is disclosed for recovering isoflavones from a soy extract comprises:

dripping the soy extract dissolved in the aqueous solvent through a chromatographic column from top to bottom packed with a ground highly polar cationic exchange resin containing sulfonic acid functional groups of the formula:

$$\{MHSO_3\}\text{—Na}$$

wherein MH is the particular adsorbent resin on which the sulfonic acid functional groups are immobilized and wherein the resin is charged with sodium ions which replace the hydrogen ions of sulfonic acid, to selectively adsorb the 7-glycosyl-isoflavones directly on the sulfonate sulfur atom while the undesired proteins and glycosides other than the 7-glycosyl-isoflavones are eluted through the chromatographic column and are removed.

4 Claims, No Drawings

5,670,632

PROCESS FOR OBTAINING AN ISOFLAVONE CONCENTRATE FROM A SOYBEAN EXTRACT

FIELD OF THE INVENTION

This invention relates to a process for recovering isoflavones from a soybean extract. More particularly the invention relates to a process for isolating the isoflavones through the use of a strongly polar, sulfonic acid cationic exchange resin.

BACKGROUND OF THE INVENTION

Isoflavones which have been isolated from water-soluble extracts of soybean plants have been used as dietary supplements and in the treatment and prevention of osteoporosis. See U.S. Pat. No. 5,424,331. The isoflavones have been obtained in aglucone form as well as in 7-acetylated form and in the form of their 7-substituted glycosides. Especially important isoflavones in aglucone form include daidzein, genistein, and glycitein and in the form of the 7-glycosides include daidzin, genistin, and glycitin.

There are several known processes for the recovery of isoflavones in aglucone form and in the form of their 7-glycosides. One of these processes includes the use of an adsorbent resin that is either non-polar or slightly polar. See U.S. Pat. No. 4,428,876. In the process disclosed therein a water-soluble extract of a soy plant is obtained which contains the isoflavones mentioned hereinabove. The water-soluble extract is obtained by extracting the whole soybean plant or the flower, flower bud, fruit, seed, stalk, leaf, xylem, root, rhizome, or root nodule. The extracting solvent is preferably an aqueous alkali solution and the preferred solution is 0.4% NaOH aqueous solution.

The whole soybean plant or plant part before extraction with the aqueous alkali is preferably treated with a solvent to remove the fat therefrom. Usually the solvent is a hydrocarbon, liquid at room temperature, such as n-hexane. Following extraction, it is also advantageous to remove proteins from the soy extract by acidifying the extract to precipitate the proteins which may then be removed by centrifuge or by filtration.

What remains is the extracted soybean material containing the isoflavones in an aqueous alkali solution, or if the proteins have been removed as explained above, in an aqueous acid solution. This aqueous alkali or aqueous acid solution is then added to the top of the adsorption column and passed through the adsorption column packed with a ground apolar or slightly polar adsorbent which has been hydrated. Typical adsorbents include acrylic ester resins and styrene-vinylbenzene resins. However, no mention of ion exchange is mentioned, let alone of the strongly polar cationic sulfonic acid ion exchange resins. The isoflavones are thus adsorbed onto the apolar or slightly polar adsorbent.

Following the adsorption of the isoflavones on the apolar or slightly polar adsorbent and removal of the aqueous acid or alkali from the bottom of the adsorption column, a suitable eluent must be obtained to remove the isoflavones from the adsorbent. A typical such eluent is a polar solvent such as methanol or ethanol. Generally several volumes of such eluent are passed down through the non-polar adsorbent, and the fractions of eluent containing the isoflavones are collected. Because isoflavones and saponins are often contained in the extract, the eluent is treated with acetone, which will selectively dissolve the isoflavones leaving the insoluble saponins behind.

The problem with such methods used heretofore is that often many of the isoflavones are not adsorbed onto the non-polar or slightly polar adsorbent and therefore these useful compounds are not recovered and are lost.

OBJECT OF THE INVENTION

It is the object of the invention to develop a new way to remove isoflavones from a soybean extract by an adsorption process that is much more efficient than the processes used heretofore.

SUMMARY OF THE INVENTION

I have found that superior removal of isoflavones from such soy extracts may be achieved if in place of the heretofore used apolar or slightly polar adsorbent resins, such as the non-polar styrene-divinyl benzene resins or the slightly polar acrylic ester resins, a highly polar sulfonic acid cationic exchange resin is employed as adsorbent.

The highly polar cationic exchange resin is defined as follows:

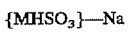

wherein MH is the particular adsorbent resin on which the sulfonic acid functional groups are supported and wherein the resin is charged with sodium ions to replace the hydrogen ions of sulfonic acid. I have found when an extract containing isoflavones, especially in the form of their 7-glycosides, is added to a solvent such as distilled water and eluted through a highly polar cationic exchange resin containing sulfonic acid functional groups, the following reaction takes place: $\{MHSO_3\}$—$Na^+$+isoflavone= $\{MHSO_3\}$-isoflavone+NaOH and more specifically $\{MHSO_3\}$—$Na_n$-(isoflavone)$_m$, where "n" and "m" stand for the stoichiometric amounts of sodium ion and isoflavone, respectively. The $\{MHSO_3\}$— is the sulfomacroanion, which, when rendered immobile on the resin, bonds especially well to the glucoside moiety at the 7-position of the 7-glycosidyl-isoflavone. It is noted that the 7-glycoside group is less hydrated than a $Na^+$.

While the desired isoflavones, especially in the form of their 7-glycosides, are selectively bound to the sulfonic acid functional groups on the adsorbent resin, where through cationic exchange the sodium cations packed in the resin are replaced by the 7-glycosidyl group of the 7-glycosidyl-isoflavones, sodium cations, undesired proteins, disconnected glycosides, are passed through the chromatographic column and recovered as a filtrate. The filtrate should not contain isoflavone.

Following the adsorption step, desorption of the isoflavone 7-glycosides from the chromatographic column containing the sulfonic acid functional groups takes place. The desorbent is an acidic aqueous alkanol containing 1 to 3 carbon atoms, preferably methanol or ethanol. The preferred desorbent is an eluent which comprises 1.0M acetic acid dissolved in an solution of aqueous ethanol. The preferred desorbent is prepared by dissolving glacial acetic acid in concentrated alcohol (e.g. 96% ethanol by volume) to obtain a desorbent that is 86% alcohol by volume containing 1.0 moles of acetic acid per liter. The desorption is preferably accomplished at a low temperature (preferably 30° C. to 35° C.) using a volume equal to 2 to 3 times the volume of the chromatographic column. Upon completion of desorption the resulting desorbents are dried using a rotor evaporator to separate same from the desired product containing the isoflavones and the desorbents are saved for subsequent use.

Thus the new process for recovering the isoflavones from a soy extract comprises the following steps:

(a) obtaining a defatted, deproteinized, soy product which is "soy molasses" or "soy solubles", an alcohol-soluble product which contains the desired isoflavones, principally in the form of their 7-glycosides as well as undesired proteins and glycosides other than the desired 7-glycosyl-isoflavones;

(b) dissolving the soy extract containing the 7-glycosyl-isoflavones and undesired proteins and glycosides other than the desired 7-glycosyl-isoflavones in an aqueous solvent;

(c) dripping the soy extract dissolved in the aqueous solvent through a chromatographic column from top to bottom packed with a ground highly polar cationic exchange resin containing sulfonic acid functional groups of the formula:

wherein MH is the particular adsorbent resin on which the sulfonic acid functional groups are immobilized and wherein the resin is charged with sodium ions which replace the hydrogen ions of sulfonic acid, to selectively adsorb the 7-glycosyl-isoflavones directly on the sulfonate sulfur atom while the undesired proteins and glycosides other than the 7-glycosyl-isoflavones are eluted through the chromatographic column and are removed; and (d) desorbing the 7-glycosyl-isoflavones from the chromatographic column packed with a ground highly polar cationic exchange resin containing sulfonic acid functional groups by eluting the chromatographic column with an acidic aqueous alkanol containing 1 to 3 carbon atoms to replace the 7-glycosyl-isoflavones bonded to the sulfonic acid functional groups with hydrogen ions.

The term "soy solubles" refers to soy components soluble an an alkanol such as methanol or ethanol.

It is important to note that the natural ratio of the soy components which are 7-glycosyl isoflavones obtained in step (a) is conserved throughout the process so that the ratio of the soy components which are 7-glycosyl isoflavones obtained after the desorption of step (d) remains the same.

Preparing the Chromatographic Column

1. The chromatographic column is assembled preferably having a volume of 20 to 25 ml taking into account the volume of the cationic exchange resin swollen with solvent.

2. Five grams of the ground cationic exchange resin containing the sulfonic acid functional groups are added to the column. Upon swelling the cationic exchange resin has a volume of 20 to 25 ml which becomes the column volume.

3. The chromatographic column may then be provided with a water jacket or other thermostat means in order to maintain the temperature between 5° and 50° C. Advantageously the water jacket is made of glass for easy observation of the process. Under no circumstances should a metal water jacket be used because the present process uses an aggressive acid medium.

4. The chromatographic column is preferably provided with a dosing apparatus for providing a supply of eluant at a certain rate. Preferably the dosing apparatus has a conical needle and a thread.

Preparation of the Cationic Resin

A highly polar cationic exchange resin containing sulfonic acid functional groups such as DOWEX® MSC-1 is employed. Other highly polar cationic exchange resins containing sulfonic acid groups may also be employed in place of DOWEX® MSC-1, including DOWEX50® DOWEX® MPC-1, DUOLITE® C-20 and IONAC® 240 all of which have sulfonic acid functional groups on a polystyrene matrix.

At the end of the 24 hour period, the volume of the grains of resin increases by 2 to 2.5 times. Thereafter the salt solution is removed and the resin is placed in 5% (approximately 1 molar) NaOH for 4 hours. After 4 hours, a fresh supply of NaOH is introduced to replace the original and replacement of the NaOH continues every 4 hours until there are no visual signs, especially color, of the liquid. The absence of color indicates a full removal of the low molecular weight cations.

The swollen grains of resin are then placed in a 20 to 25 ml column filled with distilled water. The grains are deposited in such a way that 1 to 1.5 ml of water are left with the grains. The grains of resin are also blanketed by a layer of fiberglass to prevent rising of the resin. No air bubbles may be present in the column of resin.

For preparing the freshly packed cationic resin for work, the chromatographic column is traversed alternatively by hot 3M HCl in an amount equal to 3 to 4 times the column volume and by hot water at a temperature of 40° C. in an amount equal to 4 to 5 times the column volume. The treatment is over once the colored solution stops discharging, that is when the reaction of any ferric ion present with an ammonium rhodanide probe has stopped as evidenced by no observable color in the filtrate obtained from the chromatographic column.

Thereafter all cations are washed away from the column using hot water until the acid reaction is over as indicated by a color change in methyl orange as an indicator of acidity. Subsequently all of the hydrogen cations in the resin are replaced by sodium cations which are more suitable to use in the process to bind isoflavone-7-glycosides to the sulfur atom in the sulfonic acid functional groups by the following procedure:

(a) filling the column containing the cationic resin with a 5% solution of NaOH and subsequently with a solution of 10% NaOH;

(b) completing removing hydrogen ion (pH=7.5 to 8) by submerging the resin into a base contained in the column for 2 to 3 hours each time; and (c) thereafter washing off the excess of NaOH with hot water to maintain a stable pH of 7.5 to 8.

After the cationic resin is prepared as indicated above, it is placed inside a closed vessel.

Preparation of the Solution for Adsorption

The solution for adsorption may be prepared as follows:

(a) 3 g of powdered water-soluble soy extract are dissolved in 300 ml of hot distilled water (approximately 35° C.) in a closed vessel and continuously mixed for about 3 hours. Such a concentration of the water-soluble soy extract may be varied between a 0.1% solution and a 10% solution of soy extract in the distilled water. The water-soluble soy extract may be obtained commercially or may be obtained according to the procedure set forth in U.S. Pat. No. 4,428,876.

(b) Prior to step (a) the distilled water is treated with 2N NaOH to bring the pH of the water to 9 and then during step (a) the pH of the water is regularly tested to be sure that the pH remains around 9.

(c) Optionally the mixing in step (a) and the monitoring of the pH of step (b) are continued for an additional 2 hours at ambient temperature to obtain complete dissolution of the soy extract.

(d) The solution of soy extract, which has a muddy appearance, is then either centrifuged, decanted or filtered. The sediment (Probe OC-1) left over after centrifuging is ready for an additional treatment while the supernatant solution is ready for adsorption.

In order to obtain a clear, transparent solution the pH should be 9.5 to 10. However, from a technological point of view, it is not always practical because at ambient temperature and a pH of 10, the isoflavone-7-glycosides are converted into the aglucone form of the isoflavone. The aglucone form of the isoflavone is not so easily removed by the present chromatographic adsorption process using highly polar sulfonic acid cationic exchange resins.

The Adsorption Process

The process is conducted at 15° C.±5° C.

The adsorption time for one column volume is approximately 1 hour, and generally varies from 40 to 70 minutes. A solution for adsorption is dripped from the top of the chromatographic column at a rate that corresponds to one column volume of solution per hour.

Immediately after adsorption all of the eluate filtrates obtained at the bottom of the column are selected by fractions (probes AF-1, AF-2, etc.) and are preliminarily analyzed. Usually it takes 10 to 12 column volumes to have isoflavones appear in a filtrate.

All filtrates which are selected by fractions (column volumes) are combined and evaluated for content. If the content of isoflavones in the filtrate exceeds an acceptable level, then the filtrate is returned to the top of the chromatographic column, and upon correction of the pH, is used as a replacement for the distilled water for dissolving a new portion of the soy extract.

Process of Desorption

The desorption stage follows the completion of the adsorption stage and may be conducted by using an eluent which is an acidic aqueous alkanol containing 1 to 3 carbon atoms, preferably methanol or ethanol. The preferred desorbent is an eluent which comprises the 1.0M acetic acid dissolved in an 86% solution of aqueous ethanol.

Sometime before desorption it is advantageous to carry out a cleaning of the chromatographic column.

The desorption process is carried out at a temperature of 35° C.±2° C. and at a rate of one column volume per 10 to 20 minute period.

With the exception of the first two column volumes which can be combined for analytical purposes, each subsequent column volume is considered as a fraction and separately analyzed. Based on the results of the analysis a decision can then be made as to whether additional column volumes are necessary for complete desorption of the isoflavones from the column.

Depending on the concentration of isoflavones in separate concentrated as well as dissolved fractions, the former can be gathered and dried up separately for the purpose of not losing a high degree of concentration present in the first fractions. The drying step is accomplished by using a rotor-evaporator or under vacuum at a temperature not exceeding 35° C.

The end product, depending on the drying temperature, contains a considerable amount of acetic acid which may be neutralized at an initial stage using KOH. If the drying step is conducted under more rigid conditions it is reasonable to expect an increase of acetylglucosides with respect to aglucones. If the presence of acetic acid in the end product is not desirable (even in the form of sodium acetate or potassium acetate), it is possible to use as a desorbent, a 0.1M acetic acid dissolved in an 86% solution of aqueous ethanol. Better yet methanol may be substituted for the ethanol provided the use of methanol will be acceptable in the food industry.

The advantage to using the present process with the highly polar cationic exchange resin containing sulfonic acid functional groups, such as DOWEX® MSC-1 over the process disclosed in U.S. Pat. No. 4,428,876, which employs apolar or slightly polar adsorbents, is that the recovery of isoflavones may be increased from 5 to 25 times.

The degree of the extraction of the isoflavones is calculated according to the following formula:

$$\%=B\times100/A$$

wherein

A is the initial quantity of isoflavones in the water-soluble soy extract; and

B is the amount of recovered isoflavones.

The degree of concentration of the final product is calculated as $$C\%=T\times100/N$$

where T is the weight of the isoflavones in the final product and N is the weight of the final product.

In other words according to the present process the following formula applies $$R=B\%/A\%$$

wherein

R is the factor of concentration of 7-glycosyl isoflavones, A% is the initial percent concentration of 7-glycosyl isoflavnes in the starting material of step (a) and B% is the final percent concentration of 7-glycosyl isoflavones in the product of step (d).

Adsorption processes to recover isoflavone glycosides and aglucones under the above described conditions give good results. Nevertheless, decomposition of the isoflavone glycosides to form the aglucones can have a negative effect on total adsorption. I have noticed that the adsorption of the aglucone daidzein falls behind the adsorption of the aglucone genistein. My observation of the hydrolysis of the isoflavone glycosides shows that there are approximately three times more derivatives of daidzein than derivatives of genistein in the initial recovered product. Hence it is imperative that the isoflavones as much as possible be in the form of the glycosides during both adsorption and desorption in order to obtain maximum recovery of product.

In order to maximize the amount of isoflavone in the form of the 7-glycoside, an aqueous solution of the water-soluble soy extract is kept at a pH of 8 to 10 in a refrigerator at 15° C. until the adsorption process is to begin.

During the desorption stage the rate of passing of eluents is so selected that a substantial quantity of the product is desorbed by no more than two column volumes. Then 5 to 8% of the product left over thereafter can be either fully desorbed by additional column volumes or be used in the form of diluted solutions for the initial stages of a new process for recovering the isoflavones.

I have found that the extracted water-soluble soy materials in a dry form contain isoflavones where about 95% of the isoflavones are in the form of their glycosides and only about 2 to 3% are in aglucone form. I found no evidence of coumestrol in the initial recovered product. Biochanin-A may be contained in the initial recovered product but in an amount of no more than 1%.

My research has shown that it is possible to recover approximately 2 kg of isoflavones, that is approximately 4 kg of 50% of the final product can be obtained out of 100 kg of 2% water-soluble soy extract by means of approximately 500 kg of resin over 2 days at a rate of 95%.

Technological Remarks

1. Aqueous solutions of water-soluble soy extracts in general and aqueous alkaline solutions in particular tend to ferment at ambient and higher temperatures and develop an unpleasant odor. Under certain conditions it is necessary to utilize antioxidants such as BHA, BHT (butylated hydroxytoluene) in an amount of 0.03 to 0.05% of the whole amount of solution.

2. All columns, utensils and the like should be made of materials that are not active in solutions used in technological processes.

3. The ion exchange resin used in the abovementioned technology utilizing aqueous acid or aqueous alkaline solutions does not utilize any chemicals which are prohibited for use by the food industry.

4. It is imperative that all recovered products of any given process be analyzed at an initial stage. Once the process is in progress, very little analysis is required for technological control.

5. A full hydrolysis of the isoflavones glycosides to the aglucone form is necessary to obtain a meaningful analysis of isoflavone content by means of HPLC. Thus the taking of a chromatogram of the samples before and after hydrolysis is necessary.

6. Drying of alcoholic solutions of isoflavones under vacuum can be conducted at temperatures no higher than 35° C. Higher temperatures are categorically forbidden.

7. Initial and final stages of diluting water-soluble soy extracts in aqueous alkaline solution must be so calculated that the resulting initial solution can be immediately used for adsorption before the end and without interruption of the process. Following adsorption isoflavones can be left in the closed chromatographic column for up to 24 hours at ambient temperature (20 to 22° C.) in order to ensure that the isoflavone glycosides do not ferment, especially if antioxidants have not been used.

8. Alcoholic solutions of water-soluble soy extracts in the form of isoflavone glycosides in weak acid (pH=3) even without antioxidants can be stored for a longer period of time (3 to 5 days) at ambient temperature.

9. Without reliable refrigeration equipment and without a well-ventilated storage facility with clean dry air, the preservation of wet soy extract for 5 to 10 days or even dry soy extract for 15 to 30 days is not possible.

What is claimed is:

1. A process for recovering isoflavones from a soy extract which comprises the following steps:

(a) obtaining a defatted, deproteinized soy product which is a soy molasses or soy solubles alcohol-soluble product which contains the desired isoflavones, principally in the form of their 7-glycosides as well as undesired proteins and glycosides other than the desired 7-glycosyl-isoflavones;

(b) dissolving the soy extract containing the 7-glycosyl-isoflavones and undesired proteins and glycosides other than the desired 7-glycosyl-isoflavones in an aqueous solvent;

(c) dripping the soy extract dissolved in the aqueous solvent through a chromatographic column from top to bottom packed with a ground highly polar cationic exchange resin containing sulfonic acid functional groups of the formula:

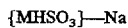
   {MHSO$_3$}—Na wherein MH is the particular adsorbent resin on which the sulfonic acid functional groups are immobilized and wherein the resin is charged with sodium ions which replace the hydrogen ions of sulfonic acid, to selectively adsorb the 7-glycosyl-isoflavones directly on the sulfonate sulfur atom while the undesired proteins and glycosides other than the 7-glycosyl-isoflavones are eluted through the chromatographic column and are removed; and (d) desorbing the 7-glycosyl-isoflavones from the chromatographic column packed with a ground highly polar cationic exchange resin containing sulfonic acid functional groups by eluting the chromatographic column with an acidic aqueous alkanol containing 1 to 3 carbon atoms to replace the 7-glycosyl-isoflavones bonded to the sulfonic acid functional groups with hydrogen ions.

2. The process for recovering isoflavones defined in claim 1 wherein according to step (c) the adsorption process is carried out at 15° C.±5° C. at a rate that corresponds to one column volume of solution per hour.

3. The process for recovering isoflavones defined in claim 1 wherein according to step (d) the desorption process is carried out at 35° C.±2° C. and at a rate of one column volume per 10 to 20 minute period.

4. The process for recovering isoflavones defined in claim 1 wherein according to step (d) the eluent is a 1.0M acetic acid dissolved in an 86% solution of aqueous ethanol prepared and by dissolving glacial acetic acid in concentrated ethanol.

* * * * *